US008590539B2

(12) United States Patent
Froissard

(10) Patent No.: US 8,590,539 B2
(45) Date of Patent: Nov. 26, 2013

(54) HEADGEAR-EARWEAR ASSEMBLY AND A METHOD OF ASSEMBLING SAME

(75) Inventor: Laurent Froissard, Cranston, RI (US)

(73) Assignee: 3M Innovative Properties Company, St. Paul, MN (US)

( * ) Notice: Subject to any disclaimer, the term of this patent is extended or adjusted under 35 U.S.C. 154(b) by 362 days.

(21) Appl. No.: 12/565,304

(22) Filed: Sep. 23, 2009

(65) Prior Publication Data

US 2010/0319715 A1 Dec. 23, 2010

Related U.S. Application Data

(60) Provisional application No. 61/219,574, filed on Jun. 23, 2009.

(51) Int. Cl.
*A61F 11/00* (2006.01)
*A61F 11/12* (2006.01)
*A61F 9/00* (2006.01)

(52) U.S. Cl.
USPC ........... 128/866; 128/864; 128/858; 351/123; 351/158; 181/135; 2/15

(58) Field of Classification Search
USPC .......... 128/864, 866; 351/123, 157, 158, 118, 351/155–156; 181/129–131, 135; 2/12, 15, 2/426, 438, 448, 209; 381/381
See application file for complete search history.

(56) References Cited

U.S. PATENT DOCUMENTS

| 3,476,467 | A | | 11/1969 | Curry | |
|---|---|---|---|---|---|
| 4,017,165 | A | * | 4/1977 | Davis | 351/153 |
| 4,347,911 | A | * | 9/1982 | Bertagna et al. | 181/130 |
| 5,074,375 | A | * | 12/1991 | Grozil | 181/135 |
| 5,475,449 | A | | 12/1995 | Pyle | |
| 5,541,677 | A | | 7/1996 | Huhtala | |
| 5,847,330 | A | * | 12/1998 | Grosslight | 181/131 |
| 5,892,564 | A | * | 4/1999 | Rahn | 351/158 |
| 6,012,612 | A | | 1/2000 | Garrett | |
| 6,012,812 | A | | 1/2000 | Rickards | |
| 6,067,664 | A | | 5/2000 | Cortes | |

(Continued)

FOREIGN PATENT DOCUMENTS

| TW | M371892 | 1/2010 |
|---|---|---|
| WO | WO 00/03287 | 1/2000 |

OTHER PUBLICATIONS

International Search Report PCT/US2010/029539, Jul. 5, 2010, 4 pgs.

*Primary Examiner* — Patricia Bianco
*Assistant Examiner* — Kari Petrik
(74) *Attorney, Agent, or Firm* — Nicole J. Einerson

(57) ABSTRACT

A headgear-earwear assembly and a method of assembling the same. The headgear-earwear assembly can include an earwear and a headgear adapted to be coupled together. The earwear can include an elongated member, such as a cord, and an earpiece coupled to the elongated member. The headgear can include a major surface and a channel oriented substantially along the major surface of the headgear. The channel can be configured to removably house at least a portion of the length of the elongated member. The headgear can further include an aperture positioned adjacent the channel and open to the channel. The aperture can include an undulating shape along at least a portion of its length. The method can include positioning at least a portion of the elongated member in the channel, such that at least a portion of the length of the elongated member is removably housed in the channel.

30 Claims, 5 Drawing Sheets

(56) References Cited

U.S. PATENT DOCUMENTS

| | | |
|---|---|---|
| 6,074,060 A | 6/2000 | Bruce |
| 6,082,855 A | 7/2000 | Fleming |
| 6,176,576 B1 | 1/2001 | Green et al. |
| 6,450,639 B1 | 9/2002 | Abraham |
| 6,604,823 B2 | 8/2003 | Hursey, Jr. |
| 6,950,531 B2 | 9/2005 | Rickards |
| 6,950,532 B1 | 9/2005 | Schumann et al. |
| 7,020,901 B2 | 4/2006 | Brhel |
| 7,133,532 B2 | 11/2006 | Rickards |
| D554,686 S | 11/2007 | Teng |
| 7,396,124 B1 | 7/2008 | Wang |
| 8,287,123 B2 * | 10/2012 | Miyashita ............ 351/123 |
| 8,472,660 B2 * | 6/2013 | Wengreen ............ 381/385 |
| 2004/0085509 A1 | 5/2004 | Lovelace |
| 2007/0236654 A1 * | 10/2007 | Skuro ............ 351/118 |
| 2009/0165189 A1 | 7/2009 | Purcell |
| 2010/0302501 A1 * | 12/2010 | Hansen ............ 351/158 |

\* cited by examiner

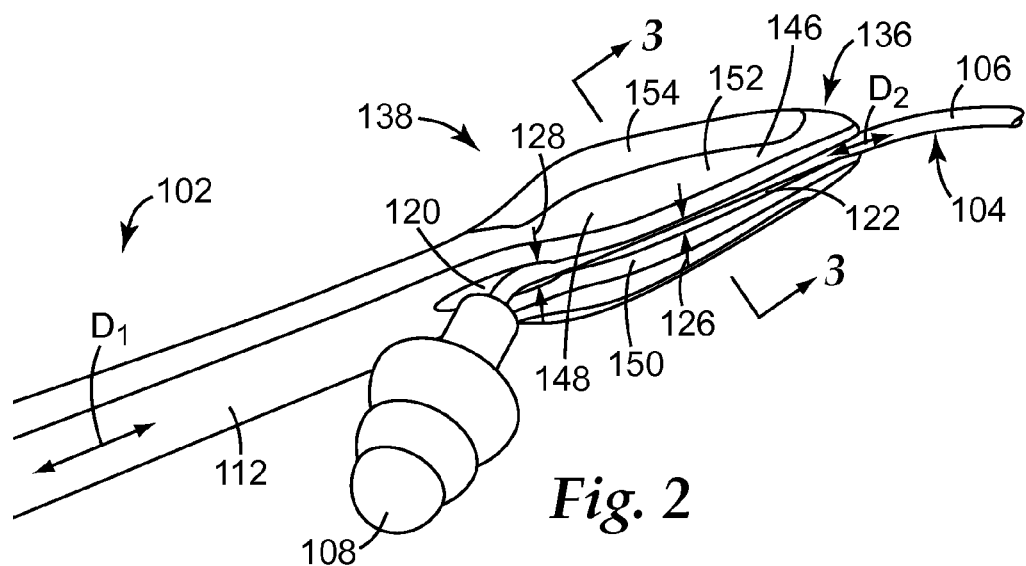
*Fig. 2*
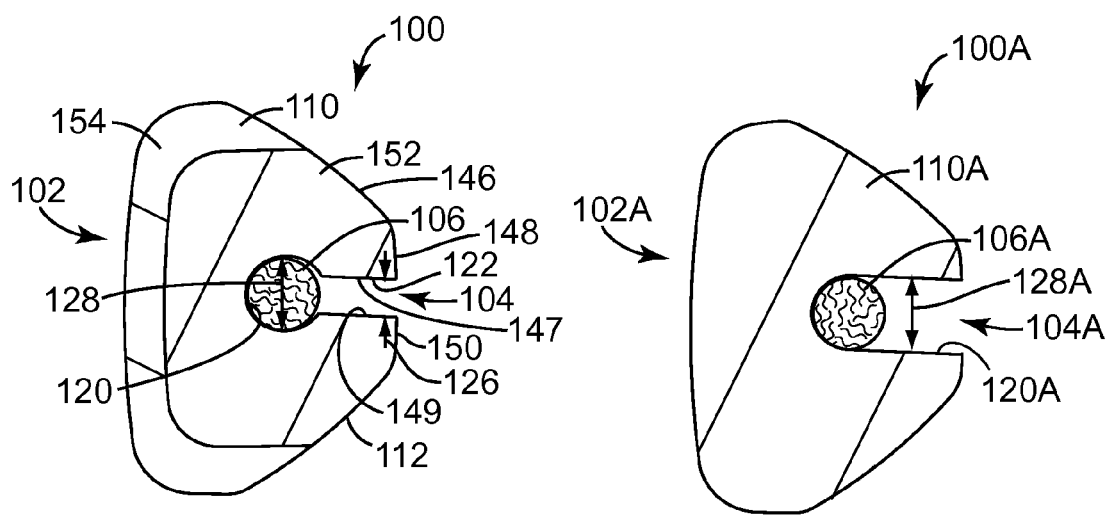
*Fig. 3*  *Fig. 3A*

HEADGEAR-EARWEAR ASSEMBLY AND A METHOD OF ASSEMBLING SAME

CROSS-REFERENCE TO RELATED APPLICATIONS

Priority is hereby claimed to U.S. Provisional Patent Application Ser. No. 61/219,574, filed Jun. 23, 2009, the disclosure of which is incorporated herein by reference in its entirety.

FIELD

The present disclosure is generally directed to a headgear-earwear assembly and a method for assembling the headgear-earwear assembly, and particularly, to a headgear-earwear assembly that allows slidable engagement between the earwear and headgear, and more particularly, to a headgear-earwear assembly in which the headgear and earwear are inhibited from becoming decoupled from one another, until desired.

BACKGROUND

In some industrial or construction settings, workers wear head, face, eye, and/or ear protective devices in order to protect their head, face and/or eyes from debris, and in order to protect their ears from excessive noise levels. In some situations, users need to protect their head, face and/or eyes, as well as their ears, all at the same time. In some situations, users may be wearing devices that cover their head, face and/or eyes, and may also be interested in receiving sound (e.g., while using communication devices, media players, etc.).

SUMMARY

Some embodiments of the present disclosure provide a headgear-earwear assembly that can include an earwear and a headgear adapted to be coupled together. The earwear can include an elongated member having a length, and an earpiece coupled to the elongated member. The headgear can include a major surface and a channel oriented substantially along the major surface of the headgear. The channel can be configured to removably house at least a portion of the length of the elongated member. The headgear can further include an aperture positioned adjacent the channel and open to the channel. The aperture can include an undulating shape along at least a portion of its length.

In some embodiments, the present disclosure provides a method of assembling a headgear-earwear assembly. The method can include providing an earwear and a headgear. The earwear can include an elongated member having a length, and an earpiece coupled to the elongated member. The headgear can include a major surface, a channel oriented substantially along the major surface of the headgear, and an aperture positioned adjacent the channel and open to the channel. The aperture can include an undulating shape along at least a portion of its length. The method can further include positioning at least a portion of the elongated member in the channel, such that at least a portion of the length of the elongated member is removably housed in the channel.

Some embodiments of the present disclosure provide a headgear-earwear assembly that can include an eyeshield, and a temple coupled to the eyeshield. The temple can include a length and a longitudinal direction oriented substantially along its length. The assembly can further include a cord having a length and a longitudinal direction oriented substantially along its length, and an earpiece coupled to the cord. The assembly can further include a channel defined by at least a portion of the temple. The channel can be oriented substantially along the longitudinal direction of the temple, and the channel can be adapted to removably house at least a portion of the length of the cord. The assembly can further include an aperture positioned adjacent the channel and open to the channel, and the aperture can include an undulating shape along at least a portion of its length.

Other features and aspects of the present disclosure will become apparent by consideration of the detailed description and accompanying drawings.

BRIEF DESCRIPTION OF THE DRAWINGS

FIG. 2 is a close-up front perspective view of the headgear-earwear assembly of FIG. 1.

FIG. 3 is a side cross-sectional view of the headgear-earwear assembly of FIGS. 1 and 2, taken along line 3-3 in FIG. 2.

FIG. 3A is a side cross-sectional view of a headgear-earwear assembly according to another embodiment of the present disclosure.

DETAILED DESCRIPTION

Figure 1:
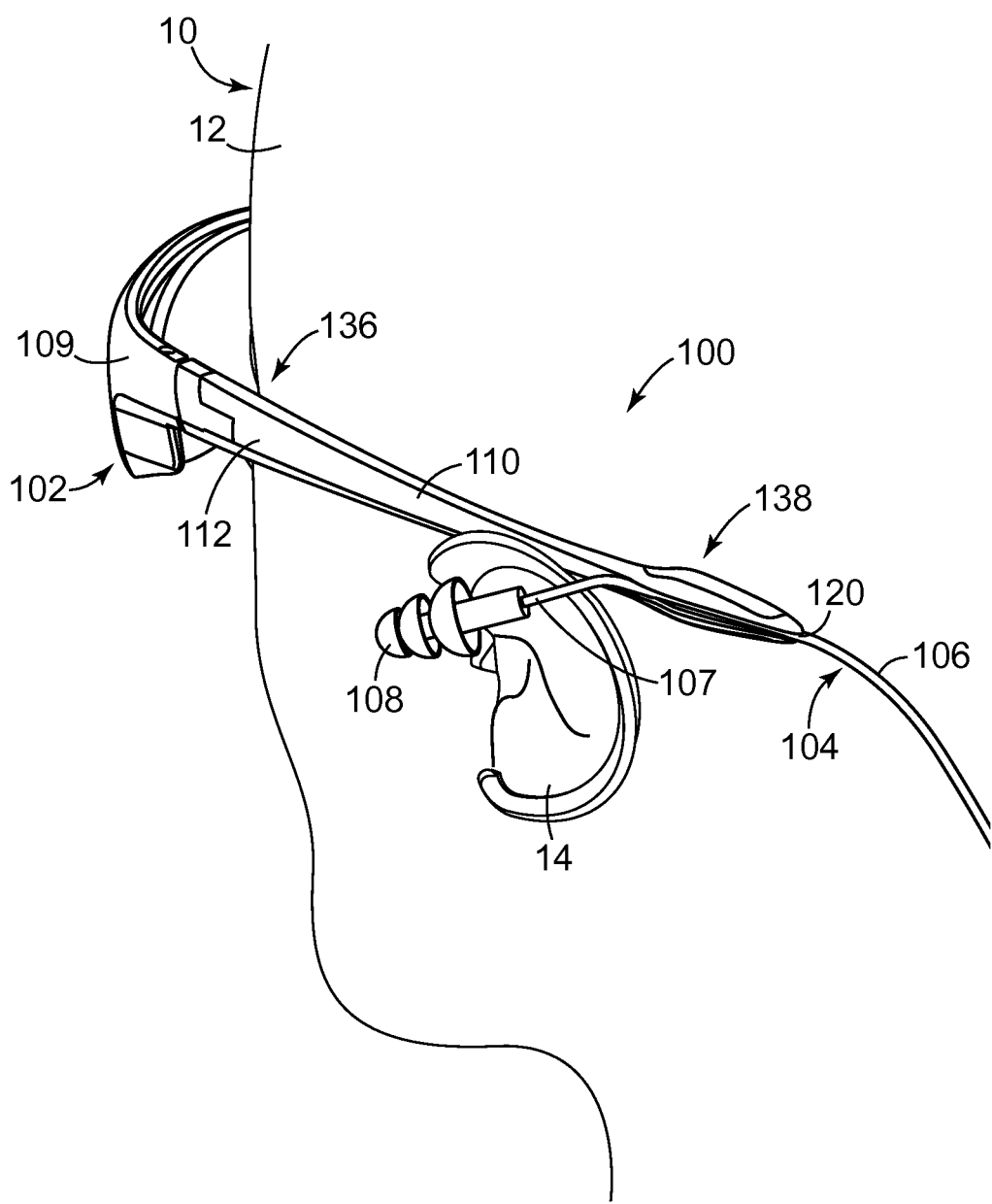
FIG. 1 is a front perspective view of a headgear-earwear assembly according to one embodiment of the present disclosure, the headgear-earwear assembly shown on the head of a user.

Before any embodiments of the present disclosure are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "assembled," and "coupled" and variations thereof are used broadly and encompass both direct and indirect assemblies and couplings. Further, "coupled" is not restricted to physical or mechanical couplings. It is to be understood that other embodiments may be utilized, and structural or logical changes may be made without departing from the scope of the present disclosure. Furthermore, terms such as "front," "rear," "top," "bottom," and the like are only used to describe elements as they relate to one another, but are in no way meant to recite specific orientations of the apparatus, to indicate or imply necessary or required orientations of the apparatus, or to specify how the invention described herein will be used, mounted, displayed, or positioned in use.

The present disclosure generally relates to a headgear-earwear assembly that includes a headgear and an earwear adapted to be removably coupled together, such that the headgear and earwear are movable with respect to one another when coupled together and are inhibited from becoming decoupled from one another under normal operating conditions.

The term "headgear" is generally used to refer to any device adapted to cover and/or be coupled to at least a portion of a user's head, face, eyes and/or ears. Such a device can be for the purpose of protection, such as from physical objects (e.g., debris), radiation (e.g., electromagnetic radiation), temperatures (e.g., hot or cold), or the like. Examples of headgear can include, but are not limited to, one or more of eyeglasses, sunglasses, safety glasses, spectacles, goggles, a faceshield, an eyeshield, a helmet, a headband, a hat, a portion thereof, or a combination thereof.

The term "earwear" is generally used to refer to any device of which at least a portion is adapted to cover and/or be coupled to a user's ears. Such a device can be for the purpose of hearing protection and/or conservation, e.g., in a noisy environment, and/or other types of protection, such as from radiation (e.g., electromagnetic radiation), noise, temperatures (e.g., hot or cold), or the like. Additionally or alternatively, such a device can be used for sound receipt and/or delivery, such as speakers that can be used with communication devices (e.g., headsets, walkie-talkies, phones, etc.) and/or media players (e.g., mp3 players, stereos, radios, etc.). Earwear can include an elongated member such as a cord, and one or more earpieces can be coupled to the cord.

The term "earpiece" is generally used to refer to the portion of earwear that is adapted to cover and/or be coupled to a user's ears. Examples of earpieces can include, but are not limited to, one or more of hearing protective and/or conservation devices (e.g., earplugs, earmuffs, earcups, etc.), sound-delivering devices (e.g., earbuds, headphones, etc.), portions thereof, or combinations thereof. In some exemplary embodiments, one or more earpieces may include a passive hearing protection and/or conservation device such as a passive earplug. In some exemplary embodiments, one or more earpieces may include an active hearing protection and/or conservation device such as active noise reduction (ANR) electronics. One or more exemplary earpieces may include a combination of passive hearing protection such as an earplug and ANR electronics.

Earpieces can be adapted to conform to the shape of a portion of a user's ear (e.g., a Eustachian tube, a concha, an auricle, an ear canal, a tragus, an antitragus, other portions of an ear, or combinations thereof). For example, an earplug can be configured to be at least partially inserted into a user's ear (e.g., at least partially into a user's ear canal). Earpieces can be formed of a variety of materials, such as materials that are durable, compressible, resilient, and/or deformable. Examples of materials that can be used to form earpieces can include, but are not limited to foams; rubbers; elastomers; polymers; earplug materials disclosed in U.S. Pat. No. RE 29,487 (Gardner, Jr.), U.S. Pat. No. 4,774,938 (Leight), U.S. Pat. No. 4,158,087 (Wood), or combinations thereof; other suitable materials; or combinations thereof.

The phrase "substantially along" is generally used to say that a first structure or direction can be oriented substantially along a second structure or in substantially the same direction as a second direction, and/or that the first structure or direction can be substantially parallel to the second structure or direction. For example, throughout the present disclosure, various structures are referred to as being oriented substantially along a surface. This can be interpreted as being on the surface, or a portion thereof, or generally parallel to the surface. In addition, throughout the present disclosure, various structures or directions are referred to as being oriented substantially along another first direction. This can be interpreted as being oriented in the same direction as the first direction, or substantially parallel to the first direction.

In some situations, users may need to cover or protect their heads, faces, and/or eyes, as well as their ears (or deliver sound to their ears), at the same time. However, in some existing environments (e.g., factory plants), head-, face- and/or eye-covering devices are located separately from one another or from earwear. As a result, workers may be tempted to wear only one device, when more than one device may be necessary for a given situation. In addition, earwear can fall out during use, causing users to lose the ear protection and/or sound delivery temporarily while they search for their earwear or while they retrieve additional earwear. The present disclosure combines one or more of head-, face- and/or ear-covering devices with earwear (e.g., ear protective devices and/or sound-delivering devices) into a single, convenient and user-friendly assembly. However, potential problems can exist, even in some assemblies that include such a combination of devices, such as the headgear and earwear becoming easily decoupled from one another under normal usage conditions, and/or the headgear and earwear being permanently or semi-permanently coupled together, so that decoupling the headgear and the earwear is too cumbersome or too difficult. The present disclosure is generally directed to an assembly that comprises a headgear-earwear combination in which the headgear and earwear are removably coupled and also inhibited from undesirably becoming decoupled.

FIGS. 1-3 illustrate a headgear-earwear assembly 100 according to one embodiment of the present disclosure. The headgear-earwear assembly 100 is shown as being positioned on a head 12 of a user 10. The headgear-earwear assembly 100 can include a headgear 102, and an earwear 104, and the headgear 102 and the earwear 104 are illustrated as being removably coupled together. The earwear 104 can include a cord 106 as an elongated member and an earpiece 108 coupled to the cord 106, and particularly, to an end 107 of the cord 106. In some embodiments, the earpiece 108 can be or can include an earplug. In some embodiments, the cord 106 can include another end to which a second earpiece can be coupled. The second earpiece can be the same as or different from the earpiece 108 coupled to the end 107 of the cord 106.

In some embodiments, as shown in FIG. 1, the cord 106 can be, can form a portion of, or can be coupled to a lanyard. Such a lanyard can be adapted to hang around a user's neck, for example, when the headgear-earwear assembly 100, or a portion thereof (e.g., the headgear 102), is not in use. In such situations, the headgear-earwear assembly 100, or a portion thereof, can be suspended from the user's neck until needed. In addition, the lanyard can be adapted to sit or hang behind a user, for example, when the headgear-earwear assembly 100, or a portion thereof, is in use. As mentioned above, the earpiece 108 can include a variety of embodiments and constructions, and the earpiece 108 is illustrated as an earplug in FIGS. 1 and 2 by way of example only.

As mentioned above, the headgear 102 can include a variety of embodiments and constructions, and in the embodiment illustrated in FIGS. 1-3, the headgear 102 is shown as including eyeglasses by way of example only. As such, the headgear 102 illustrated in FIGS. 1-3 includes an eyeshield 109 and a temple 110 coupled to the eyeshield 109 that is adapted to rest atop an ear 14 of the user 10. The headgear 102 would include a second temple positioned on the opposite side of the head 12 of the user 10, but an additional temple is not shown for simplicity and clarity. It should be understood that any description pertaining to the illustrated temple 110 can apply to another temple, or the other temple may have a different configuration.

As shown in FIG. 1, the headgear 102 can include a major surface 112. In the embodiment illustrated in FIGS. 1-3, the major surface 112 is shown as being outwardly-facing, for example, when the headgear 102 is coupled to the head 12 of the user 10. The major surface 112 can include the entire surface making up the outwardly-facing portion of the headgear 102.

As shown in FIGS. 1-3, the headgear 102, or a portion thereof, such as the temple 110, can further include a channel 120 adapted to removably house at least a portion of the length of the cord 106. As shown in FIGS. 1 and 2, the channel 120 can have a length that corresponds to the portion of the length of the cord 106 that is coupled to the headgear 102. As shown in FIGS. 1 and 2, the channel 120 can be oriented substantially along the major surface 112 of the headgear 102. In addition, as shown in FIG. 2, the channel 120 can be oriented substantially along a longitudinal direction $D_1$ of the temple 110 (i.e., along the direction in which the temple extends posteriorly from the eyeshield 109). Said another way, the channel 120 can have a longitudinal direction $D_2$ oriented substantially along its length, and the longitudinal direction $D_2$ of the channel 120 can be oriented substantially along the longitudinal direction $D_1$ of the temple 110.

As shown in FIGS. 2 and 3, the headgear 102 can further include an aperture 122 that can be positioned adjacent the channel 120 and open to (or in communication with) the channel 120. By way of example only, the aperture 122 and the channel 120 are illustrated as being outwardly-facing, which can facilitate coupling and decoupling the headgear 102 and the earwear 104, for example, while the headgear-earwear assembly 100 is positioned on the user 10. However, other configurations are possible and within the spirit and scope of the present disclosure.

In some embodiments, as shown in FIGS. 1-3, the aperture 122 can also have a length that corresponds to the portion of the length of the cord 106 that is coupled to the headgear 102. In addition, the aperture 122 can be oriented substantially along the major surface 112 of the headgear 102. Furthermore, similar to the channel 120, the aperture 122 can be oriented substantially along the longitudinal direction $D_1$ of the temple 110. Said another way, the aperture 122 can have a longitudinal direction (not shown for clarity) oriented substantially along its length, and the longitudinal direction of the aperture 122 can be oriented substantially along one or more of the longitudinal direction $D_2$ of the channel 120 and the longitudinal direction $D_1$ of the temple 110.

Furthermore, the cord 106 has a length, and a portion of its length can be positioned in the channel 120, for example, when the headgear 102 and the earwear 104 are coupled together. The cord 106 has a longitudinal direction along its length, and when the cord 106 is positioned in the channel 120 (and/or the aperture 122), the longitudinal direction of the cord 106 can be oriented substantially along the longitudinal direction $D_2$ of the channel 120 (and/or substantially along the longitudinal direction of the aperture 122), and/or substantially along the longitudinal direction $D_1$ of the temple 110. Of course, when the cord 106 is oriented substantially along the longitudinal direction $D_2$ of the channel 120 (and/or of the aperture 122), the cord 106 need not be perfectly straight. Rather, the cord 106 can include subtle waves or undulations relative to the channel 120, depending at least partly on the material makeup of the cord 106.

The cord 106 can be formed of a variety of materials, including, without limitation, fabric; polymers (e.g., PVC, recycled PVC, polycarbonate, nylon, acrylonitrile butadiene styrene (ABS), other suitable polymers, or a combination thereof); thermoplastic elastomers (e.g., Styrenic Block Copolymer, natural rubber, artificial rubber, other suitable thermoplastic elastomers, or a combination thereof); other suitable cord materials; or a combination thereof. In addition, the cord 106 can have any desired shape (e.g., cross-sectional shape) or size, which can be determined by the desired application or use of the headgear-earwear assembly 100.

The aperture 122 can serve as an entrance into the channel 120 for the cord 106. In some embodiments, as shown in FIGS. 2 and 3, the aperture 122 can have a width 126 that is less than a width 128 of the channel 120, and/or less than a width (not shown for clarity) of the cord 106. As shown in FIGS. 2 and 3, the term "width" is used to refer to a transverse dimension that is oriented substantially perpendicularly to the longitudinal direction of the respective aperture 122, channel 120 or cord 106. For example, in some embodiments, the cord 106 has a substantially round or circular cross-sectional shape, and the width or transverse dimension of the cord 106 can be the diameter of the cord 106. In some embodiments, the cord 106 is formed of a compressible material, and the aperture 122 can be configured such that the width 126 of the aperture 122 is less than the uncompressed, unaltered or original width or transverse dimension of the cord 106.

The narrower aperture 122 (i.e., narrower than one or more of the channel 120 and the cord 106) can inhibit accidental or undesirable removal of the cord 106 from the channel 120. In addition, in such embodiments, the cord 106 can be positioned in the channel 120 by positioning the cord 106 adjacent the opening to the aperture 122, and pushing at least a portion of the length of the cord 106 into the aperture 122, and then further into the channel 120. This cord position is illustrated in FIGS. 2 and 3. The method for positioning the cord 106 into the channel 120 can also include stretching the cord 106 along its length (e.g., if the cord 106 is formed of an at least somewhat elastic or elastomeric material in which the width/thickness of the cord 106 can decrease when the length of the cord 106 is increased).

As shown in FIGS. 1-3, in some embodiments, the aperture 122 can be formed in or defined by a front wall 146 of the headgear 102 (e.g., of the temple 110). By way of example only, as shown in FIGS. 2 and 3, the front wall 146 includes an upper portion 148 and a lower portion 150 that together define the aperture 122. As shown in FIG. 3, the upper portion 148 and the lower portion 150 define the aperture 122, such that the aperture is substantially straight along its length. That is, the upper and lower portion 148 and 150 each include an upper and lower surface (or wall) 147 and 149, respectively, that each at least partially defines the aperture 122. Each of the upper and lower walls 147 and 149 can be substantially straight along its respective length. In some embodiments, the upper and lower walls 147 and 149 can be flat, rounded or otherwise shaped, such that the upper and lower walls 147 and 149 need not be completely flat in the direction of the depth of the aperture 122. In some embodiments, the upper and lower walls 147 and 149 generally have a uniform cross-sectional shape, such that the aperture 122 is substantially straight and/or uniform along its length.

As shown in FIG. 3, in some embodiments, the upper and lower walls 147 and 149 can be parallel; however, in some embodiments, the upper and lower walls 147 and 149 can be arranged such that they are not parallel. For example, in some embodiments, the aperture 122 can taper along its depth, either toward or away from the channel 120. For example, in some embodiments, the upper wall 147 can be positioned a shorter distance from the lower wall 149 at a position nearer the channel 120 (i.e., toward the left-hand side of FIG. 3) and can be positioned a longer distance from the lower wall 149 at a position away from the channel 120 (i.e., toward the right-hand side of FIG. 3), or vice versa, or a combination thereof. Whether the aperture 122 is flat along its depth (i.e., toward or away from the channel 120) or tapers inwardly or outwardly along its depth, the upper portion 148 and the lower portion 150 can define a straight profile of the aperture 122, along the length of the aperture 122.

After the cord 106 has been positioned in the aperture 122 or the channel 120, the cord 106 can be slidable relative to the headgear 102, and particularly, relative to the channel 120 (and/or the aperture 122). Particularly, the cord 106 can be in sliding engagement with the channel 120 while the cord 106 is positioned in the channel 120, and while the headgear 102 and the earwear 104 are coupled together. In the embodiment illustrated in FIGS. 1-3, at least partly due to the aperture 122 having a smaller width 126 than the width of the cord 106, and/or the width 128 of the channel 120, the cord 106 can be movable with respect to the channel 120 without the cord 106 being removed from the channel 120, until desired. For example, in some embodiments, the headgear-earwear assembly 100 can be configured such that the user 10 can orient his head 12 in any orientation, and/or the cord 106 can be moved (e.g., slid) relative to the headgear 102, and the cord 106 is not removed from the channel 120 by passive external forces such as gravity or by the normal movement of the cord 106 in the channel 120.

In some embodiments, the user 10 can position the headgear-earwear assembly 100 on his head, and can then pull the earwear 104 (e.g., the earpiece 108) forward (i.e., anteriorly, toward the eyeshield 109) until the user 10 has achieved the desired length of the cord 106, and the earpiece 108 can be positioned in his ear 14. Alternatively, to reduce the amount of slack in the cord 106 that is hanging over his ear 14 (e.g., when the earpiece 108 is being used or is not being used), the user 10 can pull the posterior portion of the cord 106 in a direction away (i.e., posteriorly) from the eyeshield 109. For example, when the earpiece 108 is not being used, the cord 106 can be slid posteriorly until the earpiece 108 reaches the position shown in FIG. 2, such that the earpiece 108 is not dangling too much or is distracting or uncomfortable to the user 10.

In the embodiment illustrated in FIGS. 1-3, the cord 106 can be removed from engagement with the headgear 102, and particularly, from engagement with the channel 120, by pulling the cord 106 in the direction of the aperture 122 until the cord 106 is moved from the channel 120 into the aperture 122 and sufficient force is applied to free the cord 106 from the aperture 122 and from being coupled to the headgear 102. Removal of the cord 106 can also include stretching the cord 106 along its longitudinal direction and/or sliding the cord 106 relative to the channel 120 and/or the aperture 122.

In the embodiment illustrated in FIGS. 1-3, the width 128 and shape of the channel 120 and the width 126 and shape of the aperture 122 are shown as being relatively uniform along their respective lengths, but it should be understood that, in some embodiments, the width 128 and/or shape of the channel 120 can vary along its length. Similarly, in some embodiments, the width 126 and/or shape of the aperture 122 can vary along its length, one example of which is described in greater detail below and illustrated in FIGS. 4-8.

Moreover, the channel 120 is illustrated in FIG. 3 as having a substantially circular cross-sectional shape that is adapted to at least somewhat correspond to an outer dimension of the cord 106 (e.g., when the cord 106 has a substantially circular cross-sectional shape). However, it should be understood that, in some embodiments, the channel 120 can have any cross-sectional shape desired and need not correspond to the cross-sectional shape of the cord 106. Furthermore, in some embodiments, there can be greater clearance between the inner surface of the channel 120 and the outer surface of the cord 106 that was illustrated in FIG. 3. Similarly, the aperture 122 is shown as being substantially rectangular in cross-section, and the width 126 of the aperture 122 is sized to be slightly less than that of the width (e.g., diameter) of the cord 106, such that the cord 106 can be pressed through the aperture 122 and positioned in the channel 120 and be inhibited from being removed from the aperture 122 during normal use, until desired. However, it should be understood than any cross-sectional shape of the aperture 122 can be employed, and the present disclosure is not limited to the aperture 122 being rectangular in cross-section. In addition, the proportion of the width of the cord 106 to the width 126 of the aperture 122, the proportion of the width of the cord 106 to the width 128 of the channel 120, and the proportion of the width 126 of the aperture 122 to the width 128 of the channel 120 are shown by way of example only, and a variety of proportions can be employed. Particular utility can be achieved, however, when the width 126 of the aperture 122 is at least slightly less than the width of the cord 106.

Furthermore, in the embodiment illustrated in FIGS. 1-3, the channel 120 and the aperture 122 can be defined by at least a portion of the headgear 102. However, in some embodiments, the channel 120 and/or the aperture 122 can be formed in another element or device (e.g., a channel holder) that is then coupled to a portion of the headgear 102. Examples of such an embodiment are described in greater detail below and illustrated in FIGS. 9 and 10. In such embodiments, the channel 120 and/or the aperture 122 can still be referred to as being formed in or defined by at least a portion of the headgear 102, but it should be understood that in some embodiments, the channel 120 and/or the aperture 122 may be formed in or defined by one component that is coupled to another component of the headgear 102.

In some embodiments, as shown in FIGS. 1-3, the headgear 102, or a portion thereof, can be shaped to facilitate being handled and/or to facilitate coupling the headgear 102 and the earwear 104 together. For example, in some embodiments, the temple 110 can be shaped to facilitate handling the temple 110 and inserting the cord 106 into the channel 120 and/or the aperture 122. In some embodiments, as shown in FIGS. 1-3, the headgear 102, or a portion thereof, such as the temple 110 illustrated in FIGS. 1-3, can include a bowed outer portion 132 and a tapered end 134. Such a bowed outer portion 132 can form a gripping area and can facilitate handling the temple 110 while inserting and/or removing the cord 106 into and/or out of the channel 120 (and/or the aperture 122). Such a tapered end 134 can facilitate forcing the cord 106 through the aperture 122 and into the channel 120, and can also maintain the desired function and aesthetics of the temple 110. Still, other configurations are possible and are within the spirit and scope of the present disclosure.

Furthermore, in some embodiments, as shown in FIGS. 1-3, the headgear 102, or a portion thereof, such as the temple 110, can be formed of more than one component and/or material. For example, in some embodiments, as shown in FIGS. 1-3, in at least one position along the length of the temple 110, the temple 110 ca include a front portion 152 and a rear portion 154, and each of the front portion 152 and the second portion 154 can be formed of the same or a different material. In some embodiments, the first portion 152 can have sufficient rigidity and/or a smooth texture to allow for facile insertion and removal of the cord 106. In some embodiments, the second portion 154 can be sufficiently soft and/or resilient, such that the temple 110, or at least a portion of the temple 110 that is adjacent the channel 120, can be adapted to facilitate being handled, for example, during insertion and removal of the cord 106. Such multi-portion temples 110 can be formed by a variety of suitable manufacturing processes. For example, in some embodiments, the second portion 154 can be overmolded over the first portion 152, and the first and second portions 152 and 154 can be formed of chemically compatible materials, for example, such that they chemically bond together. Employing multi-component or multi-material elements, such as the illustrated temple 110, can also enhance the aesthetics of the headgear-earwear assembly 100, because each portion 152 or 154 can include a different color, texture, opacity, etc.

In embodiments in which the channel 120 (and, optionally, the aperture 122) is defined by at least a portion of a temple of eyeglasses, such as the temple 110 shown in FIGS. 1-3, the temple 110 can include an anterior portion or end 136 (as shown in FIG. 1) and a posterior portion or end 138 (as shown in FIGS. 1 and 2), and the channel 120 (and, optionally, the aperture 122) can be formed in the posterior portion 138.

As shown in FIGS. 1 and 2, in some embodiments, the earwear 104 can be coupled to the headgear 102, such that the earpiece 108 is positioned on the anterior side of the channel 120 when the earwear 104 and the headgear 102 are coupled together. Such configurations can facilitate sliding the cord 106 in the channel 120, particularly, when the eyeglasses are removed from the face and ears and are allowed to hang around the neck of the user 10 (e.g., when the cord 106 is, forms a portion of, or is coupled to a lanyard). However, it should be understood that the opposite configuration can also be used, such that the earpiece 108 is positioned on the posterior side of the channel 120 when the earwear 104 and the headgear 102 are coupled together.

The means for allowing insertion of and for inhibiting removal of the cord 106 from the headgear 102 is described above as a channel 120 and an aperture 122. However, in some embodiments, the entire open portion of the headgear 102 adapted to removably house the cord 106 (e.g., what was previously described as the channel 120 and the aperture 122) can be referred to as the channel 120, and the channel 120 can just be described as having a width that varies with respect to its depth. For example, the width of such a channel 120 can be narrower at its opening and the width can increase (e.g., discretely, at one position, as shown in FIG. 3, or continuously) from its open end to its closed end (e.g., the width can increase as the depth increases). Alternatively, the aperture 122 can simply be referred to as a front portion of the channel 120 that has a narrower width than a rear portion of the channel 120.

In some embodiments, however, the width 128 of the channel 120 does not change with channel depth, and such an embodiment is illustrated in FIG. 3A as headgear-earwear assembly 100A. The headgear-earwear assembly 100A is shown in cross-section, and includes a headgear 102A, which includes a temple 110A, and an earwear 104A, which includes a cord 106A. The headgear 102A further includes a channel 120A. By way of example only, the temple 110A is shown as being formed of one component or material.

As shown in FIG. 3A, the channel 120A can have a substantially constant width 128A, e.g., along its depth, and optionally along its length. In some embodiments, the cord 106 and the channel 120A can be sized to retain the cord 106A in the channel 120A until it is desired to be removed. For example, as shown in FIG. 3A, the channel 120A has the same overall depth as the combined channel 120 and aperture 122 shown in FIG. 3. By way of example only, the depth of the channel 120A is greater than the width (e.g., diameter) of the cord 106A, such that there is sufficient room for the cord 106A to be positioned far enough away from the opening to the channel 120A when the cord 106A is seated in the channel 120A that the cord 106A does not easily fall out of the channel 120A. In such embodiments, the cord 106A and the channel 120A can also be sized relative to one another, such that there is enough interference between the outer surface of the cord 106A and the inner surface of the channel 120A to allow the cord 106A and the channel 120A to be frictionally (and slidably) engaged. Such frictional engagement can still allow relative movement (e.g., sliding) between the cord 106A and the channel 120A, but can also inhibit removal of the cord 106 from the channel 120A until desired. The cord 106 can be removed from the channel 120A by supplying sufficient force to overcome the frictional forces between the cord 106 and the channel 120A.

FIGS. 4-8 illustrate a headgear-earwear assembly 200 according to another embodiment of the present disclosure, wherein like numerals represent like elements. The headgear-earwear assembly 200 shares many of the same elements and features described above with reference to the illustrated embodiment of FIGS. 1-3. Accordingly, elements and features corresponding to elements and features in the illustrated embodiment of FIGS. 1-3 are provided with the same reference numerals in the 200 series. Reference is made to the description above accompanying FIGS. 1-3 for a more complete description of the features and elements (and alternatives to such features and elements) of the embodiment illustrated in FIGS. 4-8.

The headgear-earwear assembly 200 can include a headgear 202 and an earwear 204 removably coupled together. The earwear 204 can include a cord 206 and an earpiece 208 coupled to the cord 206. The headgear 202 is illustrated as being eyeglasses and as including a temple 210 by way of example only, and the earpiece 208 is illustrated as an earplug by way of example only. The earwear 204 has been removed from FIGS. 5-7 for clarity.

The headgear 202 can include a major surface 212. In the embodiment illustrated in FIGS. 4-8, the major surface 212 is shown as being outwardly-facing, for example, when the headgear 202 is coupled to a user's head. The major surface 212 can include the entire surface making up the outwardly-facing portion of the headgear 202.

Figure 4:
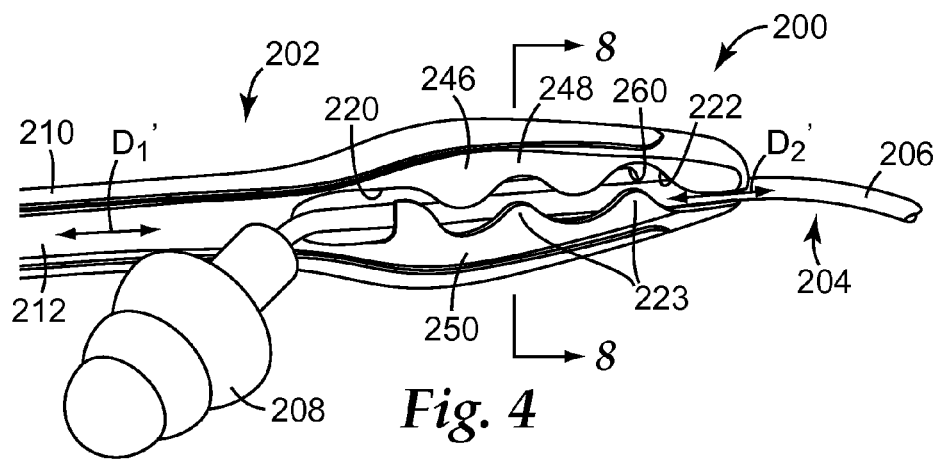
FIG. 4 is a close-up front perspective view of a headgear-earwear assembly according to another embodiment of the present disclosure, the headgear-earwear assembly including headgear and earwear.
Figure 5:
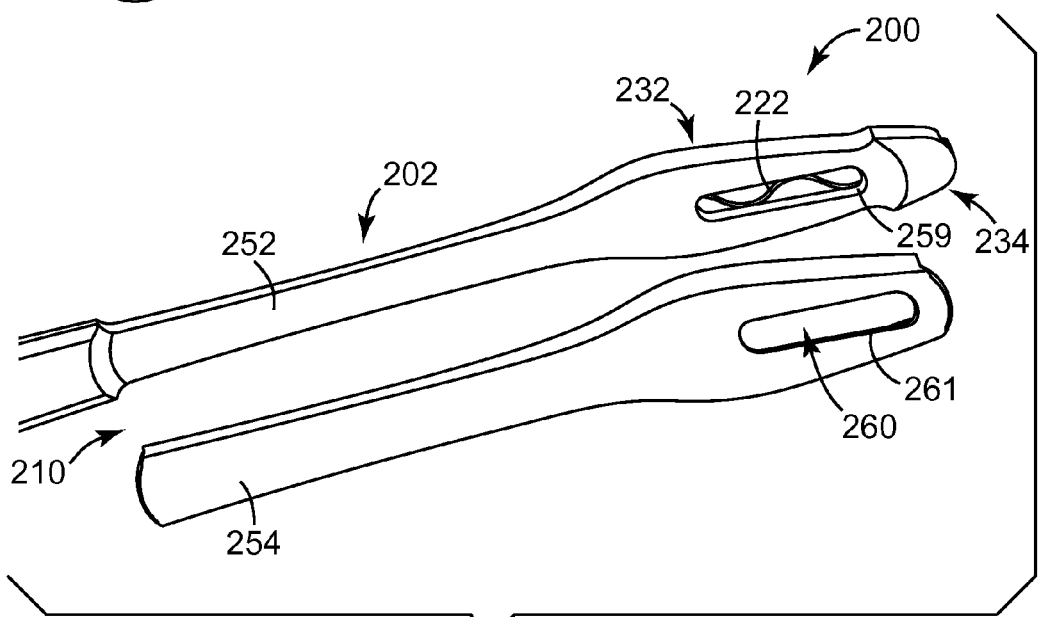
FIG. 5 is a rear exploded view of the headgear-earwear assembly of FIG. 4, with the earwear removed for clarity.

As shown in FIGS. 4-8, the headgear 202, or a portion thereof, such as the temple 210, can further include a channel 220 adapted to removably house at least a portion of the length of the cord 206. As shown in FIG. 4, the channel 220 can have a length that corresponds to the portion of the length of the cord 206 that is coupled to the headgear 202. As shown in FIG. 4, the channel 220 can be oriented substantially along the major surface 212 of the headgear 202. In addition, as shown in FIG. 4, the channel 220 can be oriented substantially along a longitudinal direction $D_1'$ of the temple 210. Said another way, the channel 220 can have a longitudinal direction $D_2'$ oriented substantially along its length, and the longitudinal direction $D_2'$ of the channel 220 can be oriented substantially along the longitudinal direction $D_1'$ of the temple 210.

As shown in FIG. 4-8, the headgear 202 can further include an aperture 222 that can be positioned adjacent the channel 220 and open to (or in communication with) the channel 220. By way of example only, the aperture 222 and the channel 220 are illustrated as being outwardly-facing, which can facilitate coupling and decoupling the headgear 202 and the earwear 204, for example, while the headgear-earwear assembly 200 is positioned on a user. However, other configurations are possible and within the spirit and scope of the present disclosure.

In some embodiments, as shown in FIGS. 4-8, the aperture 222 can also have a length that corresponds to at least a portion of the length of the cord 206 that is coupled to the headgear 202. In addition, the aperture 222 can be oriented substantially along the major surface 212 of the headgear 202. Furthermore, similar to the channel 220, the aperture 222 can be oriented substantially along the longitudinal direction $D_1$ of the temple 210. Said another way, the aperture 222 can have an overall longitudinal direction (not shown for clarity) oriented substantially along its length, and the overall longitudinal direction of the aperture 222 can be oriented substantially along one or more of the longitudinal direction $D_2'$ of the channel 220 and the longitudinal direction $D_1'$ of the temple 210.

Unlike the embodiment illustrated in FIGS. 1-3, the aperture 222 illustrated in FIGS. 4-8 is wavy, undulating or tortuous. The aperture 222 can include or be defined by a wavy, undulating or tortuous profile, and can further include or be defined by one or more undulations or projections 223 (and/or depressions or valleys, accordingly). However, the aperture 222 is still generally oriented along the major surface 212 of the headgear 202, and the aperture 222 still has a general longitudinal direction that is oriented substantially along one or more of the longitudinal direction $D_2'$ of the channel 220 and the longitudinal direction $D_1'$ of the temple 210.

Such an undulating or tortuous aperture 222 can allow relatively facile insertion of the cord 206 into the channel 220, and can also inhibit removal of the cord 206 from the channel 220 during normal use. The undulating shape of the aperture 222 is shown in FIGS. 4-8 by way of example only, but it should be understood that any suitable tortuous (e.g., undulating) shape (e.g., a sinusoidal wave, a square wave, a wave formed by only one projection 223 rather than a plurality of projections 223, other suitable wave shapes, or combinations thereof) can be employed within the spirit and scope of the present disclosure. As a result, any suitably shaped projections 223 can be employed to form the desired aperture shape.

In addition, in some embodiments in which the aperture 222 is defined by two or more projections 223, the aperture 222 can include regular and/or uniform projections 223. However, in some embodiments, the projections 223 need not all have the same shape or size, but rather can be irregular, random, and/or non-uniform. Moreover, whether the aperture 222 is defined by one or more projections 223, the "undulating shape" of the aperture 222 need not undulate equally in one direction as it does in the other direction, and the term "undulating" should not be limited to uniform wave shapes.

Figure 6:
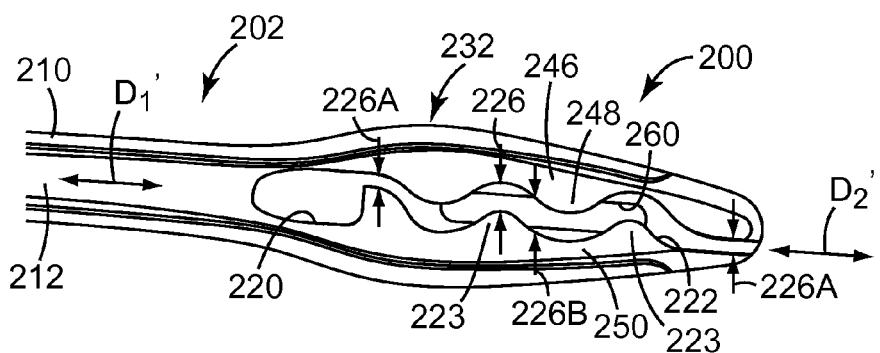
FIG. 6 is a front view of the headgear-earwear assembly of FIGS. 4 and 5, with the earwear removed for clarity.
Figure 7:
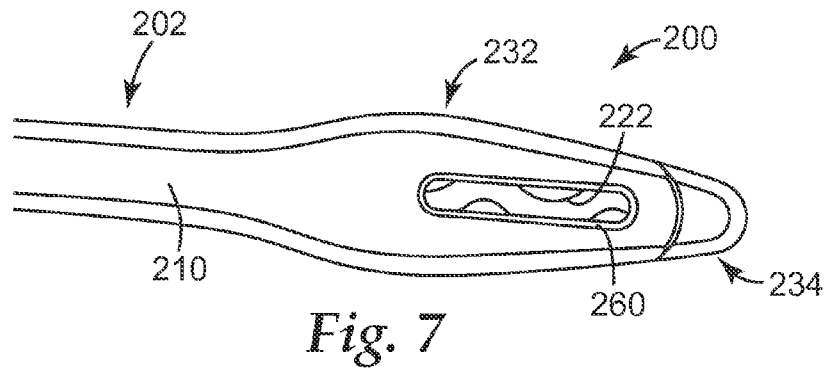
FIG. 7 is a rear view of the headgear-earwear assembly of FIGS. 4-6, with the earwear removed for clarity.

As shown in FIG. 4, in embodiments such as the headgear-earwear assembly 200, the cord 206 can be positioned behind a front wall 246 of the temple 210 when the cord 206 is positioned in the channel 220, and the aperture 222 can be formed in or defined by the front wall 246. For example, as shown in FIGS. 4 and 6, the front wall 246 includes an upper portion 248 and a lower portion 250 that together define the tortuous aperture 222 (and, accordingly, the projections 223). However, in some embodiments, only one of the upper portion 248 and the lower portion 250 include the one or more projections 223. As a result, in some embodiments, the aperture 222 can include (or be defined by) an undulating upper or lower surface and a substantially flat lower or upper surface, respectively. That is, in the embodiment illustrated in FIGS. 4-8, the upper portion 248 and the lower portion 250 both contribute to the undulating profile of the aperture 222, but this need not be the case. Said another way, in some embodiments, one or both of the upper portion 248 and the lower portion 250 can include one or more projections 223. In some embodiments in which both the upper portion 248 and the lower portion 250 both include projections 223, the projections 223 formed by the upper portion 248 can cooperate with depressions or reciprocal projections 223 in the lower portion 248, or vice versa. That is, in some embodiments, the projections 233 formed by the upper portion 248 can correspond with depressions or valleys (or spaces between adjacent projections 223) of the lower portion 250, such that the projections 223 formed by the upper portion 248 can be staggered with the projections formed by the lower portion 250.

In some embodiments, the projections 223 of the aperture 222 are more extreme than what is depicted in the embodiment illustrated in FIGS. 4-8. That is, in some embodiments, the aperture 222 oscillates further across the width of the temple 220 and the angle between adjacent projections 223 is less than what is depicted in FIGS. 4-8. However, in such embodiments, the aperture 222 (and its longitudinal direction or length) can still be considered to extend along the major surface 212 of the headgear 202, along the longitudinal direction $D_1'$ of the temple 210, and/or along the longitudinal direction $D_2'$ of the channel 220.

In addition, in some embodiments, the aperture 222 can include fewer or more projections 223 than what is shown in FIGS. 4-8. By way of example only, the aperture 222 shown in FIGS. 4-8 includes about 2.5 projections 223. However, it should be understood that fewer or more projections 223 can be employed, and that more projections 223 may make insertion of the cord 206 into the channel 220 more difficult but may improve retention of the cord 206 during use. Alternatively, fewer projections 223 may facilitate insertion of the cord 206 into the channel 220, but may reduce the ability of the headgear 102 to retain the cord 206.

Furthermore, the cord 206 has a length, and a portion of its length can be positioned in the channel 220, for example, when the headgear 202 and the earwear 204 are coupled together. The cord 206 has a longitudinal direction along its length that is coupled to the headgear 202, and when the cord 206 is positioned in the channel 220 (and/or the aperture 222), the longitudinal direction of the cord 206 can be oriented substantially along the longitudinal direction $D_2'$ of the channel 220 (and/or substantially along the longitudinal direction of the aperture 222). Of course, when the cord 206 is positioned in the channel 220 (e.g., behind the front wall 246 of the temple 210) and oriented substantially along the longitudinal direction $D_2'$ of the channel 220 (and/or of the aperture 222), the cord 206 need not be perfectly straight. Rather, the cord 206 can include subtle waves or undulations itself relative to the channel 220, depending at least partly on the material makeup of the cord 206.

Figure 11:
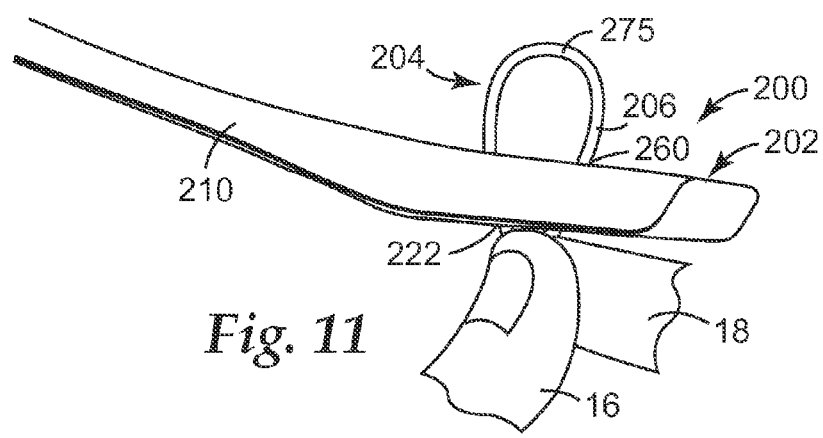
FIGS. 11 and 12 illustrate a method for assembling the headgear-earwear assembly according to one embodiment of the present disclosure.
Figure 12:
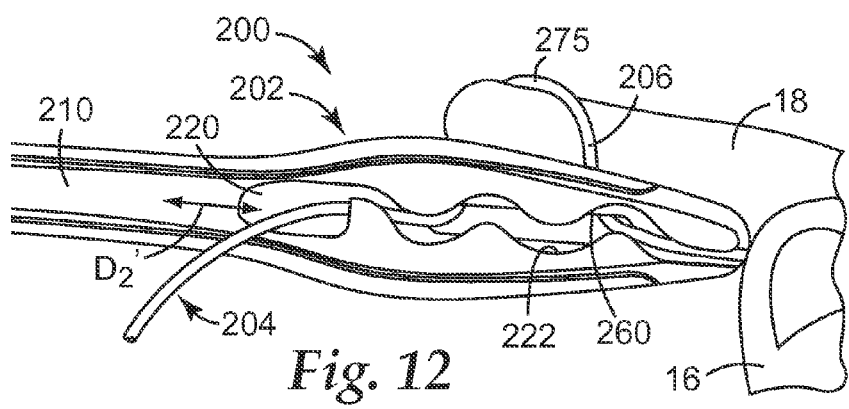

Similar to the aperture 122 described above with respect to FIGS. 1-3, the aperture 222 can serve as an entrance into the channel 220 for the cord 206. One exemplary method for inserting the cord 206 into the channel 220 is described in greater detail below and is illustrated in FIGS. 11 and 12.

Figures 8, 8A:
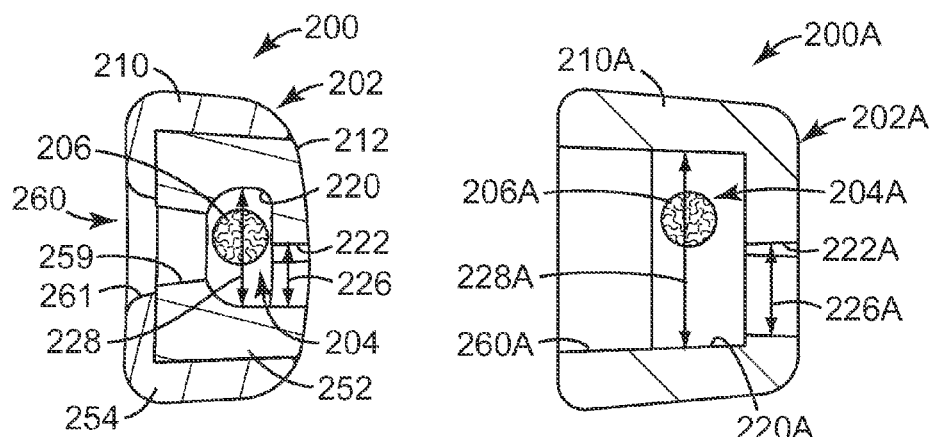
FIG. 8 is a side cross-sectional view of the headgear-earwear assembly of FIGS. 4-7, taken along line 8-8 of FIG. 4.
FIG. 8A is a cross-sectional view of a headgear-earwear assembly according to another embodiment of the present disclosure.

As shown in FIGS. 6 and 8, in some embodiments, the aperture 222 can have a width 226, and at least a portion of the width 226 can be less than a width 228 of the channel 220. In addition, at least a portion of the width 226 can be less than a width (e.g., a diameter) of the cord 206. Such a proportion between at least a portion of the width 226 of the aperture 222 and the width (e.g., diameter) of the cord 206 can enhance the retention of the cord 206 in the channel 220 during use and can function to further inhibit accidental or undesirable removal of the cord 206 from the channel 220.

In some embodiments, as shown in FIG. 6, the width 226 of the aperture 222 can vary along the length of the aperture 222. For example, in some embodiments, the width 226 of the aperture 222 can be narrowest toward the ends of the aperture 222 and widest toward the middle of the aperture 222. By way of example only, as shown in FIG. 6, the aperture 226 can include a first, narrower width 226A toward the ends of the apertures 222, and a second, wider width 226B toward the lengthwise center of the aperture 222. The varying width 226 (e.g., with width 226A and 226B) can serve to facilitate insertion of the cord 206 into the channel 220 (and/or the aperture 222) while inhibiting removal of the cord 206 from the channel 220 (and/or the aperture 222). The varying width 226 is shown by way of example only; however, it should be understood that a variety of aperture width configurations can be employed to facilitate insertion and inhibit removal of the cord 206. Additionally, or alternatively, in some embodiments, the width 226 of the aperture 222 can vary along the depth of the aperture 222.

After the cord 206 has been positioned in the aperture 222 or the channel 220, the cord 206 can be slidable relative to the headgear 202, and particularly, relative to the channel 220 (and/or the aperture 222). Particularly, the cord 206 can be in sliding engagement with the channel 220 while the cord 206 is positioned in the channel 220, and while the headgear 202 and the earwear 204 are coupled together. In the embodiment illustrated in FIGS. 4-8, at least partly due to the aperture 222 having a smaller width 226 than the width 228 of the channel 220 (and the width of the cord 206), the cord 206 can be movable with respect to the channel 220 without the cord 206 being removed from the channel 220, until desired.

Similar to the embodiment illustrated in FIGS. 1-3, the cord 206 can be removed from engagement with the headgear 202, and particularly, from engagement with the channel 220, by pulling the cord 206 in the direction of the aperture 222 (and optionally threading the cord 206 back out of the aperture 222, and past the projections 223 that define or form the aperture 222) until the cord 206 is moved from the channel 220 into the aperture 222 and sufficient force is applied to free the cord 206 from the aperture 222 and from being coupled to the headgear 202. Removal of the cord 206 can also include stretching the cord 206 along its longitudinal direction and/or sliding the cord 206 relative to the channel 220 and/or the aperture 222. In order to remove the cord 206 from being coupled to the headgear 202, in some embodiments, the cord 206 can be pulled from one end only, and in some embodiments, the cord 206 can be pulled from both ends.

In the embodiment illustrated in FIGS. 4-8, channel 220 is illustrated as being generally ellipsoidal in cross-section (see FIG. 8), and the width 228 and shape of the channel 220 are shown as being relatively uniform along its length. However, it should be understood that the channel 220 can include any cross-sectional shape, and that, in some embodiments, the width 228 and/or shape of the channel 220 can vary along its length.

Similar to the embodiment illustrated in FIGS. 1-3, the headgear 202, or a portion thereof, can be shaped to facilitate being handled and/or to facilitate coupling the headgear 202 and the earwear 204 together. For example, in some embodiments, the temple 210 can be shaped to facilitate handling the temple 210 and inserting the cord 206 into the channel 220 and/or the aperture 222. In some embodiments, as shown in FIGS. 4-8, the headgear 202, or a portion thereof, such as the temple 210, can include a bowed outer portion 232 and a tapered end 234 (see FIGS. 5-7). Such a bowed outer portion 232 can form a gripping area and can facilitate handling the temple 210 while inserting and/or removing the cord 206 into and/or out of the channel 220 (and/or the aperture 222). Such a tapered end 234 can facilitate forcing the cord 206 through the aperture 222 and into the channel 220. Still, other configurations are possible and are within the spirit and scope of the present disclosure.

Furthermore, in some embodiments, as shown in FIGS. 4-8, the headgear 202, or a portion thereof, such as the temple 210, can be formed of more than one component and/or material. For example, in some embodiments, as shown in FIGS. 4-8, in at least one position along the length of the temple 210, the temple 210 can include a front portion 252 and a rear portion 254, and each of the front portion 252 and the second portion 254 can be formed of the same or a different material. In some embodiments, the first portion 252 can have sufficient rigidity and/or smooth texture to allow for facile insertion and removal of the cord 206. In some embodiments, the second portion 254 can be sufficiently soft and/or resilient, such that the temple 210, or at least a portion of the temple 210 that is adjacent the channel 220, can be adapted to facilitate being handled, for example, during insertion and removal of the cord 206. Such multi-portion temples 210 can be formed by a variety of suitable manufacturing processes. For example, in some embodiments, the second portion 254 can be overmolded over the first portion 252, and the first and second portions 252 and 254 can be formed of chemically compatible materials, for example, such that they chemically bond together. Employing multi-component or multi-material elements, such as the illustrated temple 210, can also improve the aesthetics of the headgear-earwear assembly 200, because each portion 252 or 254 can include a different color, texture, opacity, etc.

As shown in FIGS. 4-8, in some embodiments, the headgear 202, for example, the temple 210 can include a second aperture 260. The second aperture 260 can also be adjacent the channel 220 and can open to (or be in communication with) the channel 220. In some embodiments, as shown in the embodiment illustrated in FIGS. 4-8, the second aperture 260 can be positioned opposite the channel 220 of the aperture 222 (see, for example, FIG. 8). The second aperture 260 can also be referred to as a "rear aperture," and can be used to pass the cord 206 all the way through the temple 210, for example, to facilitate insertion of the cord 206 into the channel 220, which will be described in greater detail below with reference to FIGS. 11 and 12.

As mentioned above, the embodiment illustrated in FIGS. 4-8 includes a front portion 252 and a rear portion 254 by way of example only. As a result, in some embodiments, the front portion 252 can include a first rear aperture 259, and the rear portion 254 can include a second rear aperture 261, that together define the full rear aperture 260 (see FIGS. 5 and 8). While the rear aperture 260 can facilitate insertion of the cord 206 into the channel 220, the rear aperture 260 is not necessary in all embodiments, and is only shown by way of example only. In some embodiments, the front portion 252 and the rear portion 254 can be configured such that the front portion 252 defines the aperture 222, the rear portion 254 defines the rear aperture 254, and the front portion 252 and the rear portion 254 together define the channel 220.

As mentioned above, in some embodiments, the channel 220 can have a variety of cross-sectional shapes, including a rectangular, or another parallelpipedal (e.g., trapezoidal) cross-sectional shape. Such an embodiment is illustrated in FIG. 8A as headgear-earwear assembly 200A. The headgear-earwear assembly 200A is shown in cross-section, and includes a headgear 202A, which includes a temple 210A, and an earwear 204A, which includes a cord 206A. The headgear 202A further includes a channel 220A. By way of example only, the temple 210A is shown as being formed of one component or material, and the temple 210A and the channel 220A are both shown as having a generally trapezoidal cross-sectional shape. The aperture 222A is similar to the above-described aperture 222 illustrated in FIGS. 4-8.

Similar to the embodiment illustrated in FIGS. 4-8, the width 226A of the aperture 222A is less than the width 228A of the channel 220A. However, by way of example only, the ratio of the of the aperture width 226A of the channel width 228A is less than the ratio of the aperture width 226 to the channel width 228 illustrated in FIGS. 4-8.

In addition, the headgear 202A, and particularly, the temple 210A includes a rear aperture 260A that is formed by the single component temple 210A. By way of example only, the rear aperture 260A is also illustrated in FIG. 8A as having a generally trapezoidal cross-sectional shape.

Figure 9:
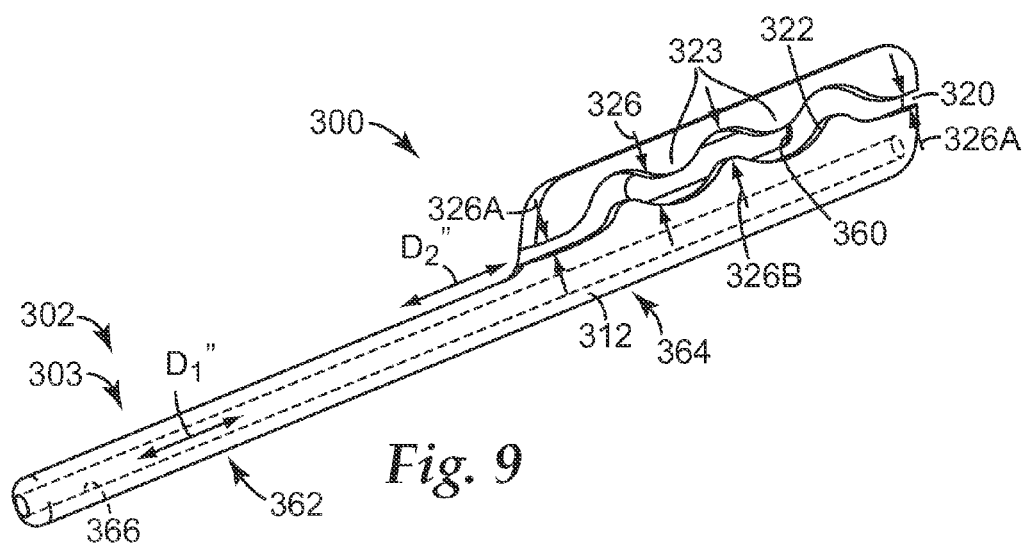
FIG. 9 is a front perspective view of a headgear-earwear assembly according to another embodiment of the present disclosure.

FIG. 9 illustrates a headgear-earwear assembly 300 according to another embodiment of the present disclosure, wherein like numerals represent like elements. The headgear-earwear assembly 300 shares many of the same elements and features described above with reference to the illustrated embodiment of FIGS. 4-8. Accordingly, elements and features corresponding to elements and features in the illustrated embodiment of FIGS. 4-8 are provided with the same reference numerals in the 300 series. Reference is made to the description above accompanying FIGS. 4-8 for a more complete description of the features and elements (and alternatives to such features and elements) of the embodiment illustrated in FIG. 9.

The headgear-earwear assembly 300 can include a headgear 302 and an earwear that can be removably coupled together. The earwear of the headgear-earwear assembly 300 is not shown in FIG. 9 for clarity, but any earwear described herein can be employed with the headgear-earwear assembly 300. In the embodiment illustrated in FIG. 9, the headgear 302 includes (or can be coupled to) a channel holder 303, and the channel holder 303 includes a channel 320 and an aperture 322, similar to the channel 220 and the aperture 222 described above and illustrated in FIGS. 4-8. That is, the channel 320 is adapted to removably house a cord of an earwear, and the aperture 322 includes projections 323 that allow a cord to be inserted into the channel 320, while inhibiting undesired removal of the cord from the channel 320 during use. By way of example only, the aperture 322 includes about three projections or undulations 323, but it should be understood that the aperture 322 can instead include the same configuration as the aperture 222 shown in FIGS. 4-8, or the aperture 322 can include another configuration.

In some embodiments, as shown in FIG. 9, the channel holder 303 can further include a second, or rear, aperture 360, which can be used to facilitate loading a cord into the channel 320.

As shown in FIG. 9, the channel holder 303 can include a first portion 362 that is adapted to be coupled to another portion of the headgear 302, and a second portion 364 that is adapted to be coupled to earwear, and, for example, to house the channel 320. In some embodiments, the first portion 362 and the second portion 364 can overlap, and there need not be a clear division between the two portions 362 and 364. In the embodiment illustrated in FIG. 9, the first portion 362 is elongated and is adapted to be coupled to a temple (e.g., such as the temple 110 or temple 210) of a pair of eyeglasses. Particularly, by way of example only, the first portion 362 includes a central bore 366 that is shaped and dimensioned to receive at least a portion of a temple of a pair of eyeglasses. That is, in some embodiments, the channel holder 303 can include a "temple tip" that is adapted to form the end of a temple of eyeglasses. For example, in some embodiments, the temple tip can be coupled to an end of a metal temple.

As shown in FIG. 9, the second portion 364 can be positioned posteriorly relative to the first portion 362, such that when the channel holder 303 is coupled to a temple, the second portion 364 can be positioned above and/or slightly behind a user's ear (see, for example, FIG. 1). Such an arrangement or configuration can allow earwear to be easily accessed while the headgear-earwear assembly 300 is in use, without interfering with the normal operation of the headgear 302 or the earwear. However, it should be understood that a variety of arrangements can instead be employed.

As further shown in FIG. 9, the headgear 302, and particularly, the channel holder 303, can include a major surface 312, and the channel 320 can be oriented substantially along the major surface 312. In addition, the headgear 302, or a portion thereof, such as a temple, or the channel holder 303, can further include a longitudinal direction $D_1''$, and the channel 320 can be oriented substantially along the longitudinal direction $D_1''$. Said another way, the channel 320 can have a longitudinal direction $D_2''$ oriented substantially along its length, and the longitudinal direction $D_2''$ of the channel 320 can be oriented substantially along the longitudinal direction $D_1''$ of the headgear 302/channel holder 303/temple.

In addition, the aperture 322 can also be oriented substantially along the major surface 312 of the headgear 302 and/or the channel holder 303. Furthermore, the aperture 322 can be oriented substantially along the longitudinal direction $D_1''$. Said another way, the aperture 322 can have a longitudinal direction (not shown for clarity) oriented substantially along its length, and the longitudinal direction of the aperture 322 can be oriented substantially along one or more of the longitudinal direction $D_2''$ of the channel 320 and the longitudinal direction $D_1''$ headgear 302/channel holder 303/temple.

In some embodiments, as shown in FIG. 9, the width 326 of the aperture 322 can vary along the length of the aperture 322. For example, in some embodiments, the width 326 of the aperture 322 can be narrowest toward the ends of the aperture 322 and widest toward the middle of the aperture 322. By way of example only, as shown in FIG. 9, the aperture 326 can include a first, narrower width 326A toward the ends of the apertures 322, and a second, wider width 326B toward the lengthwise center of the aperture 322. Additionally, or alternatively, in some embodiments, the width 326 of the aperture 322 can vary along the depth of the aperture 322.

In some embodiments, the headgear 302, or a portion thereof, such as the second portion 364 of the channel 303, can be shaped to facilitate being handled and/or to facilitate coupling the headgear 302 and earwear together. For example, in some embodiments, as shown in FIG. 9, the second portion 364 can be wider than the first portion 362. In addition, it should be understood that any of the additional details or alternatives of the embodiments described in FIGS. 1-8 can also be applied to the embodiment illustrated in FIG. 9, such as a bowed and tapered shape, being formed of multiple components or materials, etc.

Figure 10:
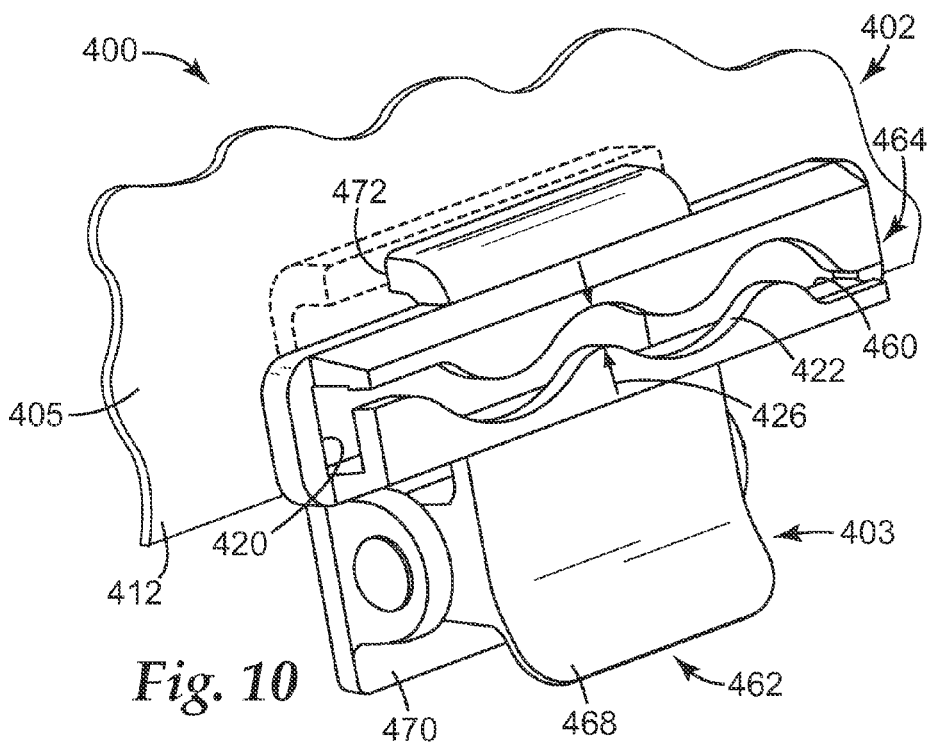
FIG. 10 is a front perspective view of a headgear-earwear assembly according to another embodiment of the present disclosure.

FIG. 10 illustrates a headgear-earwear assembly 400 according to another embodiment of the present disclosure, wherein like numerals represent like elements. The headgear-earwear assembly 400 shares many of the same elements and features described above with reference to the illustrated embodiments of FIGS. 4-9. Accordingly, elements and features corresponding to elements and features in the illustrated embodiments of FIGS. 4-9 are provided with the same reference numerals in the 400 series. Reference is made to the description above accompanying FIGS. 4-9 for a more complete description of the features and elements (and alternatives to such features and elements) of the embodiment illustrated in FIG. 10.

The headgear-earwear assembly 400 can include a headgear 402 and an earwear that can be removably coupled together. The earwear of the headgear-earwear assembly 400 is not shown in FIG. 10 for clarity. In the embodiment illustrated in FIG. 10, the headgear 402 includes (or can be coupled to) a channel holder 403, and the channel holder 403 includes a channel 420 and an aperture 422 that are similar to the channel 220 and the aperture 222 described above and illustrated in FIGS. 4-8. That is, the channel 420 is adapted to removably house a cord of an earwear, and the aperture 422 includes an undulating profile that allows a cord to be inserted into the channel 420 while inhibiting undesired removal of the cord from the channel 420 during use. By way of example only, the aperture 422 includes about 2.5 projections or undulations 423, similar to the aperture 222 shown in FIGS. 4-8 and described above. However, it should be understood that the aperture 422 can instead include the same configuration as the aperture 322 shown in FIG. 9, or another configuration.

As shown in FIG. 10, in some embodiments, the channel holder 403 can be in the form of a clip, such that the channel holder 403 can be clipped to another portion 405 of the headgear 402. For example, in some embodiments, the headgear 402 can include a headband, or a faceshield, and the channel holder 403 can be clipped onto the portion 405 of such a headband or faceshield in a desired position or orientation. Of course, any of the above-described headgear configurations can be employed, and the channel holder 403 can be configured to be coupled to any portion thereof. As such, FIG. 10 illustrates one example of an embodiment in which the channel holder 403 can easily be removably or reversibly coupled to the portion 405 of the headgear 402. In such embodiments, the channel holder 403 can be moved by each individual user to a position that is comfortable, non-distracting, and useful to that user. In addition, the channel holder 403 can be decoupled from the portion 405 during use, if necessary.

In some embodiments, the channel holder 403 can include a first portion 462 that is adapted to be coupled to the portion 405 of the headgear 402 and which is shown in FIG. 10 as including a clip. The channel holder 403 can further include a second portion 464 that is adapted to be coupled to earwear, and, for example, to house the channel 420. The first portion 462 and the second portion 464 can be formed of the same or different materials. For example, in some embodiments, the first portion 462 of the channel holder 403 may need to be formed of a material that allows the first portion 462 to be reliably coupled to the portion 405 of the headgear 402 without causing any damage to the headgear 402. The second portion 464 of the channel holder 403 may need to be formed of a material that is suitably rigid and/or smooth to maintain the structural integrity of the channel 420 and/or aperture 422.

As shown in FIG. 10, the first portion 462 can include a front clip portion 468 and a rear clip portion 470, at least upper portions of which are biased toward one another. The biasing force (e.g., which can be provided by a spring or other suitable structure) can be overcome by squeezing the lower portions of the front clip portion 468 and the rear clip portion 470 toward one another, thereby widening an opening 472 between upper portions of the front and rear clip portions 468 and 470, such that the portion 405 of the headgear 402 can be positioned intermediately of the front and rear clip portions 468 and 470 (i.e., in the opening 472).

In addition, similar to the channels 220 and 320 described above and shown in FIGS. 4-8 and 9, respectively, the channel 420 can be oriented substantially along a major surface 412 of the headgear 402. The major surface 412 can be formed by the channel holder 403, a portion of the headgear 402 to which the channel holder 403 is coupled, or combinations thereof. Furthermore, as described above with respect to the apertures 222 and 322, the aperture 422 can have a varying width 426 and can be narrowest at its ends and widest at its center. Furthermore, the channel holder 403 can further include a second, or rear, aperture 460, which can be used to facilitate loading a cord into the channel 420.

In addition, it should be understood that any of the additional details or alternatives of the embodiments described in FIGS. 1-9 can also be applied to the embodiment illustrated in FIG. 10, such as a bowed and tapered shape, being formed of multiple components or materials, etc.

FIGS. 11 and 12 illustrate a method of assembling a headgear-earwear assembly. The method illustrated in FIGS. 11 and 12 will be described with respect to the headgear-earwear assembly 200 illustrated in FIGS. 4-8 by way of example only. However, it should be understood that the method can be used to load a cord into any of the headgear-earwear systems 200, 200A, 300 and 400 described herein that employ a wavy aperture 222, 222A, 322 and 422 and a rear aperture 260, 260A, 360 and 460.

As shown in FIG. 11, the cord 206 can be grasped (e.g., between a thumb 16 and forefinger 18) and formed into a loop 275, which can be fed through the aperture 222, through the channel 220 and out the rear aperture 260. As shown in FIG. 12, the loop 275 can be held behind the headgear 202 (e.g., the temple 210), for example, by placing the forefinger 18 through the loop 275. In addition, the loop 275 can be pulled further out of the rear aperture 260, as necessary. While the loop 275 (or a portion of the cord 206) is held in place, the cord 206 can be pulled to the side(s) (e.g., by the thumb 16), which can cause the cord 206 to be threaded through the aperture 222 and loaded into the channel 220, as shown in FIG. 12. The same action can be performed on the other side (e.g., simultaneously or sequentially) to complete the loading of the cord 206 into the channel 220.

That is, as shown in FIG. 12, positioning the cord 206 into the channel 220 can include orienting the longitudinal direction of the cord 206 substantially along the longitudinal direction $D_2'$ of the channel 220. In addition, positioning the cord 206 into the aperture 222 and/or channel 220 can include stretching the cord 206 (e.g., lengthwise) prior to inserting the cord 206 or as the cord 206 is inserted into the aperture 222 and/or the channel 220.

As mentioned above, the same method can be used to assemble the headgear-earwear systems 300 and 400. The method for assembling such embodiments can further include coupling the channel holder 303, 403 to another portion (e.g., 405) of the headgear 302, 402. For example, in some embodiments, coupling the channel holder 303 to another portion of the headgear 302 can include coupling the first portion 362 of the channel holder 303 to a temple of a headgear 302. In some embodiments, coupling the channel holder 403 to the portion 405 of the headgear 402 can include clipping the channel holder 403 to the portion 405.

The method illustrated in FIGS. 11 and 12 and described above is included by way of example only; however, the present disclosure is not limited to this method of assembly, and other methods are within the spirit and scope of the present disclosure.

The embodiments described above and illustrated in the figures are presented by way of example only and are not intended as a limitation upon the concepts and principles of the present disclosure. As such, it will be appreciated by one having ordinary skill in the art that various changes in the elements and their configuration and arrangement are possible without departing from the spirit and scope of the present disclosure. Various features and aspects of the present disclosure are set forth in the following claims.

What is claimed is:

1. A headgear-earwear assembly comprising:
   an earwear, the earwear including
      an elongated member having a length, and
      an earpiece coupled to the elongated member; and
   a headgear including an eyeshield, the headgear and the earwear adapted to be coupled together, the headgear having a major surface and including
      a channel oriented substantially along the major surface of the headgear, the channel configured to removably house at least a portion of the length of the elongated member in sliding engagement with the channel, such that the elongated member is movable along a longitudinal direction of the channel when the earwear and the headgear are coupled together, and
      an aperture positioned adjacent the channel and providing an entrance to the channel for the elongated member, the aperture having an undulating shape along at least a portion of its length.

2. The headgear-earwear assembly of claim 1, wherein the aperture is defined by at least one projection, and wherein the aperture is formed in a wall that includes a first portion and a second portion, and wherein at least one of the first portion and the second portion includes the at least one projection.

3. The assembly of claim 2, wherein the first portion includes at least one first projection, wherein the second portion includes at least one second projection, and wherein the at least one first projection is staggered with respect to the at least one second projection, the at least one first projection and the at least one second projection positioned to at least partially form the undulating shape of the aperture.

4. The assembly of claim 2, wherein the first portion and the second portion of the wall together define at least a portion of the aperture, and wherein at least one of the first portion and the second portion includes an undulating profile.

5. The assembly of claim 1, wherein the earpiece includes an earplug.

6. The assembly of claim 1, wherein the headgear includes a channel holder coupled to another portion of the headgear, and wherein the channel is defined by at least a portion of the channel holder.

7. The assembly of claim 6, wherein the channel holder is removably coupled to another portion of the headgear.

8. The assembly of claim 6, wherein the channel holder includes a clip that is adapted to be clipped to another portion of the headgear.

9. The assembly of claim 1, wherein the channel has a substantially rectangular cross-sectional shape.

10. The assembly of claim 1, wherein the aperture includes a width, and wherein the width of the aperture varies along its length.

11. The assembly of claim 1, wherein the aperture includes a first end and a second end, and wherein the width of the aperture tapers toward at least one of the first end and the second end.

12. The assembly of claim 1, wherein the aperture is a first aperture, and wherein the headgear includes a second aperture positioned adjacent the channel and open to the channel.

13. The assembly of claim 12, wherein the second aperture is opposite the channel from the first aperture.

14. The headgear-earwear assembly of claim 1, wherein the headgear includes at least one of eyeglasses, sunglasses, safety glasses, spectacles, goggles, a face shield, a helmet, and a combination thereof.

15. A method of assembling a headgear-earwear assembly, the method comprising:
   providing an earwear, the earwear including
      an elongated member having a length, and
      an earpiece coupled to the elongated member;
   providing a headgear including an eyeshield, the headgear having a major surface and including
      a channel oriented substantially along the major surface of the headgear,
      an aperture positioned adjacent the channel and providing an entrance to the channel for the elongated member, the aperture having an undulating shape along at least a portion of its length;
   coupling the headgear and the earwear together by positioning at least a portion of the elongated member in the channel, such that at least a portion of the length of the elongated member is removably housed in the channel and in sliding engagement with the channel; and
   sliding the elongated member along a longitudinal direction of the channel when the earwear and the headgear are coupled together.

16. The method of claim 15, wherein the headgear includes a channel holder coupled to another portion of the headgear, and wherein the channel is defined by at least a portion of the channel holder, and further comprising coupling the channel holder to another portion of the headgear.

17. The method of claim 16, wherein coupling the channel holder to another portion of the headgear includes removably coupling the channel holder.

18. The method of claim 16, wherein coupling the channel holder to another portion of the headgear includes clipping the channel holder to another portion of the headgear.

19. The method of claims 15, wherein the aperture is a first aperture, and wherein the headgear further includes a second aperture positioned adjacent the channel and open to the channel, and further comprising:
   forming a loop in the elongated member; and
   threading the loop of the elongated member into the first aperture, into the channel, and out the second aperture.

20. The method of claim 19, further comprising holding the loop outside of the second aperture and threading the elongated member through the first aperture to load the elongated member into the channel.

21. The method of claim 19, wherein the second aperture is positioned opposite the channel from the first aperture.

22. A headgear-earwear assembly, the assembly comprising:
   an eyeshield;

a temple coupled to the eyeshield, the temple having a length and a longitudinal direction oriented substantially along its length;

a cord having a length and a longitudinal direction oriented substantially along its length;

an earpiece coupled to the cord;

a channel defined by at least a portion of the temple, the channel oriented substantially along the longitudinal direction of the temple, wherein the channel is adapted to removably house at least a portion of the length of the cord; and an aperture positioned adjacent the channel and providing an entrance to the channel for the cord, the aperture having an undulating shape along at least a portion of its length.

23. The assembly of claim 22, wherein the eyeshield is formed by at least one of goggles, glasses, spectacles, and a combination thereof.

24. The assembly of claim 22, wherein the earpiece includes an earplug.

25. A headgear-earwear assembly comprising:

an earwear, the earwear including
   an elongated member having a length, and
   an earpiece coupled to the elongated member; and a headgear including an eyeshield, the headgear and the earwear adapted to be coupled together, the headgear having a major surface and including
   a channel having a longitudinal direction oriented substantially along a longitudinal direction of the major surface of the headgear, the channel configured to removably house at least a portion of the length of the elongated member in sliding engagement with the channel, such that the elongated member is movable along the longitudinal direction of the channel when the earwear and the headgear are coupled together, and
   an aperture positioned adjacent the channel and providing an entrance to the channel for the elongated member, the aperture having an undulating shape along at least a portion of its length;

wherein the elongated member forms at least a portion of at least one of a cord and a lanyard.

26. A headgear-earwear assembly comprising:

an earwear, the earwear including
   an elongated member having a length, and
   an earpiece coupled to the elongated member; and a headgear including an eyeshield, the headgear and the earwear adapted to be coupled together, the headgear having a major surface and including
   a channel oriented substantially along the major surface of the headgear, the channel configured to removably house at least a portion of the length of the elongated member in sliding engagement with the channel, such that the elongated member is movable along a longitudinal direction of the channel when the earwear and the headgear are coupled together, and
   an aperture positioned adjacent the channel and providing an entrance to the channel for the elongated member, the aperture having an undulating shape along at least a portion of its length, the aperture and the channel each having a width oriented substantially perpendicular to the longitudinal direction of the channel, the width of the aperture being less than the width of the channel.

27. The assembly of claim 26, wherein the aperture is a first aperture, and wherein the headgear includes a second aperture positioned adjacent the channel and open to the channel, and located opposite the width of the channel from the first aperture.

28. A method of assembling a headgear-earwear assembly, the method comprising:

providing an earwear, the earwear including
   an elongated member having a length, and
   an earpiece coupled to the elongated member;

providing a headgear including an eyeshield, the headgear having a major surface and including
   a channel oriented substantially along the major surface of the headgear,
   an aperture positioned adjacent the channel and providing an entrance to the channel for the elongated member, the aperture having an undulating shape along at least a portion of its length, the aperture and the channel each having a width oriented substantially perpendicular to the longitudinal direction of the channel, the width of the aperture being less than the width of the channel;

coupling the headgear and the earwear together by positioning at least a portion of the elongated member in the channel via the aperture, such that at least a portion of the length of the elongated member is removably housed in the channel and in sliding engagement with the channel; and sliding the elongated member along a longitudinal direction of the channel when the earwear and the headgear are coupled together.

29. The method of claims 28 wherein the aperture is a first aperture, and wherein the headgear further includes a second aperture positioned adjacent the channel and open to the channel, and located opposite the width of the aperture of the channel from the first aperture, and further comprising:

forming a loop in the elongated member; and threading the loop of the elongated member into the first aperture, into the channel, across the width of the channel, and out the second aperture.

30. A headgear-earwear assembly, the assembly comprising:

an eyeshield;

a temple coupled to the eyeshield, the temple having a length and a longitudinal direction oriented substantially along its length;

a cord having a length and a longitudinal direction oriented substantially along its length;

an earpiece coupled to the cord;

a channel defined by at least a portion of the temple, the channel oriented substantially along the longitudinal direction of the temple, wherein the channel is adapted to removably house at least a portion of the length of the cord; and an aperture positioned adjacent the channel and providing an entrance to the channel for the cord, the aperture having an undulating shape along at least a portion of its length, the aperture and the channel each having a width oriented substantially perpendicular to the longitudinal direction of the channel, the width of the aperture being less than the width of the channel.

* * * * *

UNITED STATES PATENT AND TRADEMARK OFFICE
CERTIFICATE OF CORRECTION

PATENT NO. : 8,590,539 B2  
APPLICATION NO. : 12/565304  
DATED : November 26, 2013  
INVENTOR(S) : Laurent Froissard Page 1 of 1

It is certified that error appears in the above-identified patent and that said Letters Patent is hereby corrected as shown below:

In the Specification

Column 9
Line 9, Delete "ca" and insert -- can --, therefor.

Column 11
Line 24, Delete "$D_1$" and insert -- $D_1'$ --, therefor.

Column 15
Line 9, Delete "parallelpipedal" and insert -- parallelepipedal --, therefor.
Line 24, Before "aperture" delete "of the".

In the Claims

Column 20
Line 52, In Claim 19, delete "claims" and insert -- claim --, therefor.

Column 22
Line 33, In Claim 29, delete "claims" and insert -- claim --, therefor.

Signed and Sealed this
Twenty-seventh Day of May, 2014

Michelle K. Lee
*Deputy Director of the United States Patent and Trademark Office*